United States Patent [19]

Houlihan et al.

[11] 3,989,704
[45] Nov. 2, 1976

[54] 3-SUBSTITUTED-4-ARYL ISOQUINOLINES

[75] Inventors: William J. Houlihan, Mountain Lakes; Jeffrey Nadelson, Lake Parsippany, both of N.J.

[73] Assignee: Sandoz, Inc., E. Hanover, N.J.

[22] Filed: Jan. 21, 1975

[21] Appl. No.: 542,843

Related U.S. Application Data

[60] Division of Ser. No. 411,074, Oct. 30, 1973, Pat. No. 3,872,125, which is a continuation-in-part of Ser. No. 339,616, March 3, 1973, abandoned, which is a continuation-in-part of Ser. No. 259,860, June 5, 1972, abandoned.

[52] U.S. Cl. .................. 260/283 R; 260/283 SY; 260/289 D; 434/258
[51] Int. Cl.² ........................................ C07D 217/22
[58] Field of Search ............................. 260/283 D

[56] References Cited
UNITED STATES PATENTS

| | | | |
|---|---|---|---|
| 3,666,763 | 5/1972 | Grethe et al. | 260/289 D |
| 3,870,722 | 3/1975 | Houlihan et al. | 260/283 D |
| 3,872,125 | 3/1975 | Houlihan et al. | 260/283 D |

OTHER PUBLICATIONS

Berti et al.; Chem. Abstr. vol. 53:20063c (1958).

Berti, Chem. Abst. vol. 47; 4342c; (1951).

*Primary Examiner*—Nicholas S. Rizzo
*Assistant Examiner*—Mary C. Vaughn
*Attorney, Agent, or Firm*—Gerald D. Sharkin; Robert S. Honor

[57] ABSTRACT

3-Substituted-4-aryl isoquinolines, e.g. 3-tertiary butyl-4-phenyl-1,2,3,4-tetrahydroisoquinoline, prepared from corresponding isoquinoline intermediates, are useful as anti-diabetic agents.

2 Claims, No Drawings

3-SUBSTITUTED-4-ARYL ISOQUINOLINES

This is a division of application Ser. No. 411,074 filed Oct. 30, 1973, now U.S. Pat. No. 3,872,125, which is a continuation-in-part of application Ser. No. 339,616, filed Mar. 3, 1973, now abandoned which in turn is a continuation-in-part of application Ser. No. 259,860, filed June 5, 1972, now abandoned.

This invention pertains to 3-substituted-4-aryl isoquinolines. More particularly, it concerns 3-substituted-4-phenyl or substituted-phenyl-1,2,3,4-tetrahydroisoquinolines, intermediates and acid addition salts thereof, and processes for their preparation.

The tetrahydroisoquinolines of this invention may be represented by the following structural formula:

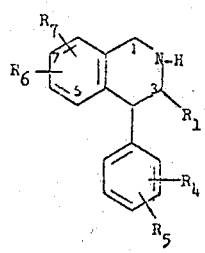

where
R₁ represents

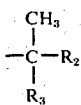

where
R₂ and R₃ are each independently methyl or ethyl, or R₂ and R₃ together represent (CH₂)ₙ
where
n represents 4, 5, or 6, and
R₄, R₅, R₆ and R₇ each independently represent hydrogen, halo of atomic weight 19–36, trifluoromethyl, lower alkyl, i.e. alkyl of 1–4 carbon atoms, e.g. methyl, ethyl, propyl, isopropyl, butyl, and the like, and lower alkoxy, i.e. alkoxy having 1–4 carbon atoms, such as methoxy, ethoxy, isopropoxy, and the like, provided that R₆ and R₇ may not represent alkyl at the 8-position, and provided further that two trifluoromethyl groups or two tert.butyl groups or a trifluoromethyl and a tertiary butyl group are not on adjacent carbon atoms.

The compounds of formula (I) are prepared by hydrogenation of corresponding isoquinoline intermediates of formula (II) according to the following reaction scheme:

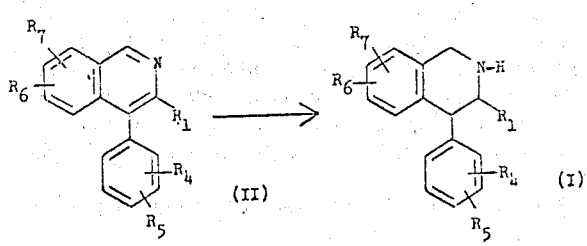

where
R₁ through R₇ and the provisos are as set out above.

Compounds (II) may be converted into compounds (I) by hydrogenating the former with a platinum metal catalyst, such as platinum oxide in inert solvent, such as loweralkanoic acid, e.g. acetic acid, at a temperature of from about 20°–60° C., preferably about 25°–35° C., at 25–100 psi until about two equivalents of hydrogen are absorbed. Neither time temperature of reaction, pressure nor the solvent used is critical.

The compounds of formula (II) represent an additional aspect of this invention and they may be prepared according to the following reaction scheme:

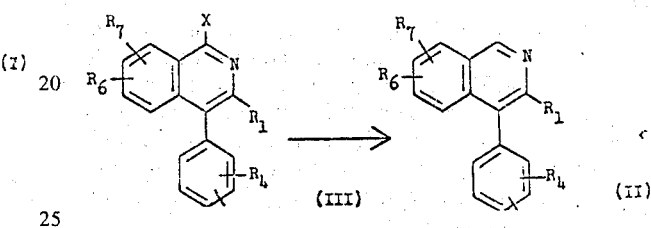

where
R₁ through R₇ and the provisos are as set out above, and
X represents halo of atomic weight about 35–80.

Compounds (II) may be prepared from compounds (III) by hydrogenating the latter at 25–100 p.s.i. in inert alcohol solvent, e.g. lower alkanols such as ethanol or isopropanol in the presence of platinum metal catalyst such as palladium, conveniently palladium on carbon, until one equivalent of hydrogen is absorbed. The hydrogenation may be performed at a temperature of about 20°–60° C., preferably about 25°–35° C. A base such as an alkali metal hydroxide, e.g. sodium hydroxide or potassium hydroxide, is desirably added to neutralize the HCl liberated in the reaction. Neither the time, temperature, pressure nor solvent utilized is critical in obtaining compounds (II).

The novel compounds of formula (III) may be obtained according to the following reaction scheme:

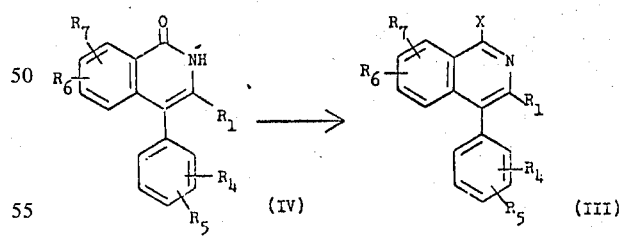

where
X, R₁ through R₇ and the provisos are as set out above.

Compounds (III) are accordingly obtained by treating a compound of formula (IV) with halogenating agent such as PCl₅, POCl₃, SOCl₂, PBr₅, PBr₃ and SOBr₂ and the like optionally in solvent such as aromatic hydrocarbon solvent, e.g. benzene or toluene, for about 30–90 minutes at a temperature of about 80°–150° C., conveniently at the reflux temperature of the system. Neither time, temperature nor solvent are critical.

The compounds (IV) are also novel and may be prepared according to the following reaction scheme:

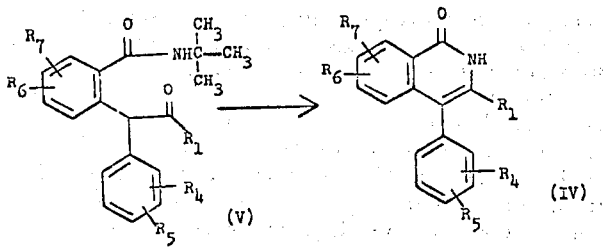

where
R₁ through R₇ and respecting compounds (IV) the provisos are as set out above, and provided further that R₆ and R₇ may not represent alkyl at a position ortho to the carbon bonded to the amido group on compounds (V), provided further that two trifluoromethyl groups or two tert.butyl groups or a trifluoromethyl and a tertiary butyl group are not on adjacent carbon atoms.

Compounds (IV) are thus prepared from compounds (V) by treating the latter with polyphosphoric acid at a temperature of about 70°–120° C., preferably about 80°–100° C., for about ½ to 3 hours. The reaction time and temperature are not critical.

As will be appreciated by persons skilled in the art, compounds (IV) and (V) may also exist in tautomeric form and the exact form of the compounds and the amount of compound in each tautomeric form will depend upon such factors as pH, temperature, solvent, etc. For simplicity, compounds (IV) and (V) will be depicted by use of the structures shown, but it will be understood that the corresponding tautomeric forms and their use and production are also contemplated by the invention.

The compounds of formula (V) may be obtained according to the following reaction scheme from compounds (VI) and compounds (VII).

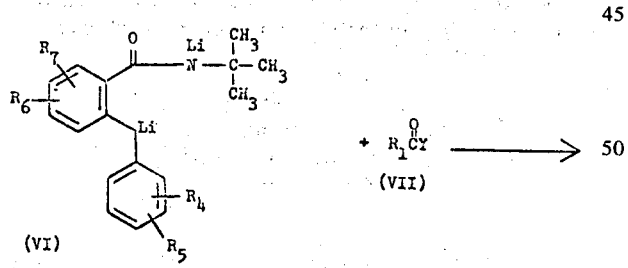

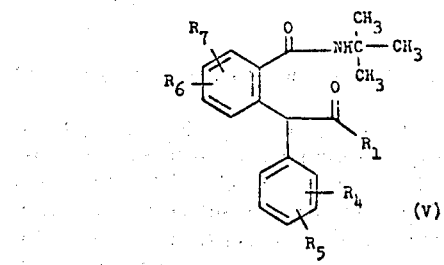

where
R₁ through R₇ and the provisos are as set out above regarding compounds (V), and
Y represents halo of atomic weight 35–80.

Compounds (VI) and (VII) are first reacted in inert solvent such as hydrocarbon solvents, e.g. benzene or toluene, or ethers such as ethyl ether or tetrahydrofuran, at a temperature of from about −60° to about 10° C. The preferred temperature range is about −20° to −50° C. and the reaction may be run for 1–10 hours. The resulting product is then hydrolyzed by conventional techniques to provide compounds (V).

The compounds of formula (VI) may be obtained from the compounds of the formula

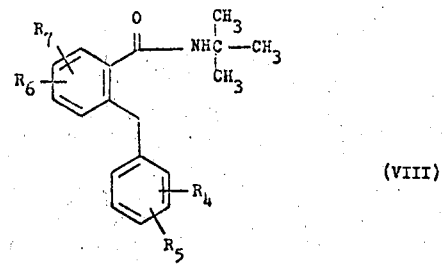

where
R₄, R₅, R₆, R₇ and the provisos are as set out above for compounds (V),
by treatment with a lithiating agent, particularly an alkyl or aryl lithium compound; n-butyl lithium is especially preferred. This reaction may be performed in solvent and for a period of time similar to that described above in connection with the process for obtaining compounds (V). The temperature of the reaction is preferably from about −10° to +10° C. Compound (VI) is normally not isolated from the reaction mixture and may be used directly in the process for preparing compounds (V) above.

The compounds (VIII) are preparable from compounds of the formula

[Structure IX]

where
R₄ through R₇ are as set out above,
provided that R₆ and R₇ may not represent alkyl at a position ortho to the carbon bonded to the acid group, and provided further that two trifluoromethyl groups or two tertiary butyl groups or a trifluoromethyl and a tertiary butyl group are not on adjacent carbon atoms, in a standard manner by halogenating compounds (IX) with halogenating agents such as thionyl chloride, and aminating the resulting acid halide with tert.butylamine.

The compounds (IX) are prepared according to the following reaction scheme:

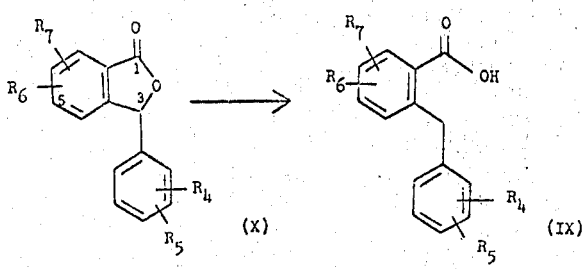

where
R$_4$ through R$_7$ and the provisos for compounds (IX) are as set out above,
provided that R$_6$ and R$_7$ on compounds (X) may not represent alkyl at the 7-position, and provided further that two trifluoromethyl groups or two tertiary butyl groups or a trifluoromethyl and a tertiary butyl group are not on adjacent carbon atoms.

Compounds (IX) are prepared from compounds (X) by hydrogenating the former with hydrogen gas in the presence of a platinum metal catalyst, preferably palladium on carbon. The hydrogenation is conveniently performed in alcoholic solvents at room temperature.

Compounds (X) may be prepared according to the following reaction scheme:

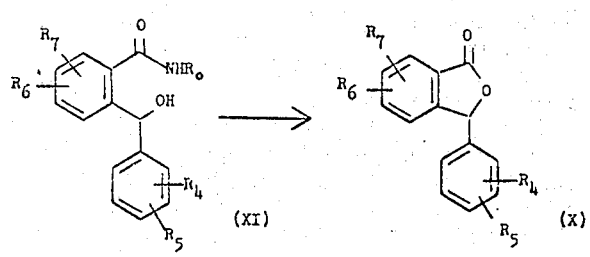

where
R$_o$ represents lower alkyl, as defined above, or phenyl, and
R$_4$ through R$_7$ are as set out above, as are the provisos respecting compounds (X), and provided that regarding compounds (XI) R$_6$ and R$_7$ do not represent alkyl at a position ortho to the carbon bonded to the amido group, and provided further that two trifluoromethyl groups or two tertiary butyl groups or a trifluoromethyl and a tertiary butyl group are not on adjacent carbon atoms.

According to the above process, compound (XI) is heated in inert hydrocarbon or halogenated hydrocarbon solvent, e.g. benzene, toluene, pentane, o-dichlorobenzene and the like. The reaction may be carried out at a temperature of about 80°–200° C., and conveniently at the reflux temperature of the solvent utilized.

The compounds of formula (XI) are obtainable from compounds (XII) according to the following reaction scheme:

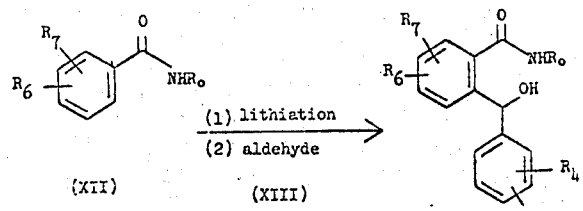

where
R$_4$ through R$_7$, R$_o$ and the provisos are as set out above for compounds (XI).

Compounds (XI) are prepared from compounds (XII) in inert hydrocarbon or ether solvent, e.g. benzene, toluene, ethyl ether, tetrahydrofuran and the like. The reaction is a two step reaction involving lithiation of the compound (XII) to obtain a dilithio intermediate thereof, which in turn is treated with an appropriately substituted benzaldehyde (XIII) to obtain compounds (XI). The lithiation is preferably performed at a temperature between about −60° to +10° C. for about 1–3 hours whereas the second step, generally performed without separation of the dilithio intermediate, is performed between −10° and +10° C. for about 1–3 hours.

Unless specifically indicated otherwise, the products of each of the reactions described above may be recovered by conventional techniques such as crystallization, filtration, trituration, and the like.

Certain of the compounds of formulae (VII), (XII) and (XIII) are known and may be prepared according to methods disclosed according to the literature. The compounds of formulae (VII), (XII) and (XIII) not specifically disclosed may be prepared by methods analogous to those in the literature from known compounds.

Compounds (I) and (II) may exist in the form of their acid addition salts. Said salts and their respective free bases may be converted from one to the other by conventional techniques and are chemically interchangeable for purposes of the above described process. The compounds of formula (I) exist in racemic form or in the form of optically active isomers. The separation and recovery of the respective isomers may be readily accomplished employing conventional techniques, and such isomers are included within the scope of the invention.

The compounds of formula (I) above are useful because they possess pharmacological properties in animals, such as mammals. In particular, the compounds may be used as anti-diabetic agents as indicated by their activity in rats orally administered active agent at a dose of 200 mg/kg of animal body weight. The rats are made diabetic by intraperitoneal injection of 250 mg/kg of alloxan monohydrate four days prior to the experiment. Only those rats showing positive reactions for sugar in urine are used. The positive reactions are as shown on "Clinistix" made by Ames Company, Division of Miles Laboratories, Inc., Elkhart, Ind. and described in U.S. Pat. Nos. 3,453,180; 3,164,534; 3,123,443; 3,050,373 and 2,981,606.

Two hours after oral administration of the drug, the rats are anesthetized by intraperitoneal injection of sodium hexobarbital (120 mg/kg). Blood is taken by incision of the jugular vein and is collected in a test tube which contains 0.1 ml. of heparin (1,000 units/ml). The heparinized blood is used to determine blood sugar level.

Anti-diabetic activity is determined by comparison of the mean blood sugar (mg %) of drug treated rats with that of controls (given vehicle two hours before sacrificing).

For such usage, the compounds of formula (I) may be combined with a pharmaceutically acceptable carrier or adjuvant, and may be administered orally in such forms as tablets, capsules, elixers, suspensions and the like, or parenterally in the form of an injectable solution or suspension. The dosage will vary depending upon the mode of administration utilized and the particular compound employed.

As indicated above, the compounds of formula (I) may be similarly administered in the form of their non-toxic pharmaceutically acceptable acid addition salts. Such salts possess the same order of activity as the free base, are readily prepared by reacting the base with an appropriate acid and accordingly are included within the scope of the invention. Representative of such salts are the mineral salts, such as hydrochloride, hydrobromide, sulfate, phosphate and the like and the organic acid salts, such as the succinate, benzoate, acetate, p-toluenesulfonate, benzenesulfonate and the like.

As noted above, the compounds of formula (I) exist as optical isomers. In some cases, greater pharmacological activity or other beneficial attribute may be found for a particular isomer and in such instances administration of such isomer may be employed.

In general, satisfactory results are obtained when the compounds (I) are administered at a daily dosage of from about 4–400 mg/kg of animal body weight, preferably orally and in divided doses, 2 to 4 times a day or in sustained release form. For most larger mammals (e.g. primates) the total daily dosage is from about 250–2000 mg. per day. Dosage forms suitable for internal use comprises from about 60 mg. to about 1000 mg. of the active compound in intimate admixture with a solid or liquid pharmaceutically acceptable carrier or diluent.

Tablets containing 100 mg. of active ingredient and 250 mg. of lactose may be prepared by conventional techniques and are useful in treating diabetes at a dose of one tablet 2 to 4 times a day.

EXAMPLE 1

N-tert.butyl-α-phenyl-o-toluamide

To a flask equipped with a stirrer, dropping funnel, condenser and gas inlet tube maintained under a nitrogen atmosphere there is added at room temperature 67.5 g. (0.5 mole) N-methyl benzamide and 1200 ml. dry tetrahydrofuran. The reaction flask is immersed in an ice bath and cooled to an internal temperature of 5° C. Stirring is initiated and 688 ml. of 1.6 M. n-butyl lithium (1.1 mole) in hexane is added dropwise over about 1 hour maintaining temperature below 8° C. The resulting dilithio salt is stirred at 5° C. for an additional hour and then a solution of 58.5 g. (0.55 mole) of benzaldehyde in 500 ml. tetrahydrofuran is added dropwise in about 1 hour maintaining the temperature between −10° to +10° C. The resulting mixture is stirred at 5° C. for 1 hour longer and 300 ml. of saturated ammonium chloride is added maintaining the temperature at about 10° C. The layers are separated and the organic phase dried over anhydrous magnesium sulfate, filtered and evaporated in vacuo to give α-hydroxy-N-methyl-α-phenyl-o-toluamide.

A mixture of 76.5 g. of α-hydroxy-N-methyl-α-phenyl-o-toluamide and (0.314 mole) 150 ml. o-dichlorobenzene is heated at reflux for 18 hours. The mixture is cooled and filtered and the resulting solid triturated with cold ether to give 3-phenyl phthalide.

When the above process is carried out and in place of benzaldehyde there is used
  a. p-chlorobenzaledhyde,
  b. o-tolualdehyde,
  c. p-methoxybenzaldehyde,
  d. m-trifluoromethylbenzaldehyde,
  e. 3,4-dichlorobenzaldehyde, or
  f. p-tolualdehyde
there is obtained through the corresponding intermediate α-hydroxy-N-methyl-o-toluamide,
  a. 3-p-chlorophenyl phthalide,
  b. 3-o-tolyl phthalide,
  c. 3-p-methoxyphenyl phthalide,
  d. 3-m-trifluoromethylphenyl phthalide,
  e. 3-(3,4-dichlorophenyl) phthalide, or
  f. 3-p-tolyl phthalide, respectively.

When the above detailed procedure is carried out and in place of N-methyl benzamide there is used 1
  g. o-chloro-N-phenyl benzamide,
  h. N-methyl-p-toluamide,
  i. N-methyl-m-trifluoromethyl benzamide, or
  j. p-methoxy-N-methyl benzamide,
there is obtained through the corresponding intermediate α-hydroxy-α-phenyl-o-toluamide,
  g. 7-chloro-3-phenyl phthalide,
  h. 5-methyl-3-phenyl phthalide,
  i. 6-trifluoromethyl-3-phenyl phthalide, or
  j. 5-methoxy-3-phenyl phthalide, respectively.

A mixture of 55.2 g. of 3-phenyl phthalide (0.263 mole), 600 ml. ethanol and 5.9 g. of 10% Pd/C is hydrogenated at room temperature and 50 psi until 1 equivalent of $H_2$ is absorbed. The catalyst is removed by filtration and the solvent removed in vacuo and the residue triturated in petroleum ether to give α-phenyl-o-toluic acid; m.p. 101°–104° C.

To a mixture of 49.8 g. (0.235 mole) α-phenyl-o-toluic acid, 300 ml. ether and 10 ml. pyridine, add dropwise with stirring 25 ml. (0.35 mole) of thionyl chloride. The resulting mixture is stirred 21 hours at room temperature then filtered and the solvent removed in vacuo. The resulting acid chloride is dissolved in 150 ml. ether and added dropwise to 35.7 g (0.48 mole) of tert.butylamine in 500 ml. of ethyl ether, and the mixture cooled to 0° C. After addition is complete the resulting mixture is stirred 1 hour at room temperature, the layers separated, the ether washed with 100 ml. of water, 100 ml. of 2N sodium hydroxide and then with water again, dried over magnesium sulfate, filtered and evaporated to give N-tert.butyl-α-phenyl-o-toluamide; m.p. 91°–92° C.

When the procedure described in the above two paragraphs is carried out and in place of 3-phenyl phthalide there is used
  a. 3-p-chlorophenyl phthalide,
  b. 3-o-tolyl phthalide,
  c. 3-p-methoxyphenyl phthalide,
  d. 3-m-trifluoromethylphenyl phthalide,
  e. 3-(3,4-dichlorophenyl) phthalide,
  f. 3-p-tolyl phthalide,
  g. 7-chloro-3-phenyl phthalide,
  h. 5-methyl-3-phenyl phthalide,
  i. 6-trifluoromethyl-3-phenyl phthalide, or
  j. 5-methoxy-3-phenyl phthalide,
there is obtained through the corresponding acid and acid halide,
  a. α-(p-chlorophenyl)-N-tert.butyl-o-toluamide,
  b. N-tert.butyl-α-(o-tolyl)-o-toluamide,
  c. α-(p-methoxyphenyl)-N-tert.butyl-o-toluamide,
  d. N-tert.butyl-α-(m-trifluoromethylphenyl)-o-toluamide,
  e. α-(3,4-dichlorophenyl)-N-tert.butyl-o-toluamide,
  f. N-tert.butyl-α-(p-tolyl)-o-toluamide,
  g. 6-chloro-N-tert.butyl-α-phenyl-o-toluamide,
  h. N-tert.butyl-4-methyl-α-phenyl-o-toluamide, i. N-tert.butyl-α-phenyl-5-trifluoromethyl-o-toluamide, or
j. 4-methoxy-N-tert.butyl-α-phenyl-o-toluamide, respectively.

EXAMPLE 2

N-tert.butyl-α-phenyl-α-pivaloyl-o-toluamide

To a flask equipped with a stirrer, dropping funnel, condenser and gas inlet tube and maintained under a nitrogen atmosphere there is added at room temperature 59 g. (0.221 mole) of N-tert.butyl-α-phenyl-o-toluamide in 1000 ml. dry tetrahydrofuran. The flask is immersed in an ice bath and cooled to an internal temperature of 5° C. Stirring is initiated and 336.5 ml. (0.490 mole) of n-butyl lithium (15% in hexane) is added dropwise in about 1 hour maintaining the temperature below 8° C. The resulting solution is stirred 2 hours at room temperature, cooled to 5° C., and 26.6 g. (0.221 mole) of pivaloyl chloride in 250 ml. of dry tetrahydrofuran is added dropwise maintaining temperature below 8° C. After addition, the mixture is stirred 2 hours at room temperature and hydrolyzed with 150 ml. of saturated ammonium chloride, the resulting solution is filtered and the layers separated. The organic layer is dried over magnesium sulfate, filtered and evaporated in vacuo. The residue is triturated with ether to give N-tert.butyl-α-phenyl-α-pivaloyl-o-toluamide; m.p. 157°–161° C.

When the above process is carried out and in place of N-tert.butyl-α-phenyl-o-toluamide there is used
a. α-(p-chlorophenyl)-N-tert.butyl-o-toluamide,
b. N-tert.butyl-α-(o-tolyl)-o-toluamide,
c. α-(p-methoxyphenyl)-N-tert.butyl-o-toluamide,
d. N-tert.butyl-α-(m-trifluoromethylphenyl)-o-toluamide,
e. α-(3,4-dichlorophenyl)-N-tert.butyl-o-toluamide,
f. N-tert.butyl-α-(p-tolyl)-o-toluamide,
g. 6-chloro-N-tert.butyl-α-phenyl-o-toluamide,
h. N-tert.butyl-4-methyl-α-phenyl-o-toluamide,
i. N-tert.butyl-α-phenyl-5-trifluoromethyl-o-toluamide, or
j. 4-methoxy-N-tert.butyl-α-phenyl-o-toluamide, there is obtained
a. α-(p-chlorophenyl)-N-tert.butyl-α-pivaloyl-o-toluamide,
b. N-tert.butyl-α-pivaloyl-α-(o-tolyl)-o-toluamide,
c. α-(p-methoxyphenyl)-α-pivaloyl-N-tert.butyl-o-toluamide,
d. N-tert.butyl-α-pivaloyl-α-(m-trifluoromethylphenyl)-o-toluamide,
e. α-(3,4-dichlorophenyl)-N-tert.butyl-α-pivaloyl-o-toluamide,
f. N-tert.butyl-α-pivaloyl-α-(p-tolyl)-o-toluamide,
g. 6-chloro-N-tert.butyl-α-pivaloyl-α-phenyl-o-toluamide,
h. N-tert.butyl-4-methyl-α-pivaloyl-α-phenyl-o-toluamide, l
i. N-tert.butyl-α-pivaloyl-α-phenyl-5-trifluoromethyl-o-toluamide, or
j. 4-methoxy-N-tert.butyl-α-pivaloyl-α-phenyl-o-toluamide, respectively.

When the above process is carried out and in place of pivaloyl chloride there is used 2,2-dimethylbutanol chloride or 1-methyl cyclohexanecarbonylbromide, there is obtained
k. α-(2,2-dimethylbutanoyl)-N-tert.butyl-α-phenyl-o-toluamide, or
l. N-tert.butyl-α-(1-methyl cyclohexanoyl)-α-phenyl-o-toluamide, respectively.

EXAMPLE 3

3-tert.butyl-4-phenyl isocarbostyril

In portions 79 g. (0.225 mole) of N-tert.butyl-α-phenyl-α-pivaloyl-o-toluamide is added to 1130 mg. of polyphosphoric acid heated to 90° C. The mixture is stirred 1½ hours at 90° C. and poured onto ice with stirring. The resulting solid is filtered and washed thoroughly with water. The solid is recrystallized from chloroform: ethyl ether (1:1) to give 3-tert.butyl-4-phenyl-isocarbostyril; m.p. 284°–286° C.

when the above process is carried out and in place of N-tert.butyl-α-phenyl-α-pivaloyl-o-toluamide there is used
a. α-(p-chlorophenyl)-N-tert.butyl-α-pivaloyl-o-toluamide,
b. N-tert.butyl-α-pivaloyl-α-(o-tolyl)-o-toluamide,
c. α-(p-methoxyphenyl)-α-pivaloyl-N-tert.butyl-o-toluamide,
d. N-tert.butyl-α-pivaloyl-α-(m-trifluoromethylphenyl)-o-toluamide,
e. α-(3,4-dichlorophenyl)-N-tert.butyl-α-pivaloyl-o-toluamide,
f. N-tert.butyl-α-pivaloyl-α-(p-tolyl)-o-toluamide,
g. 6-chloro-N-tert.butyl-α-pivaloyl-α-phenyl-o-toluamide,
h. N-tert.butyl-4-methyl-α-pivaloyl-α-phenyl-o-toluamide,
i. N-tert.butyl-α-pivaloyl-α-phenyl-5-trifluoromethyl-o-toluamide, or
j. 4-methoxy-N-tert.butyl-α-pivaloyl-α-phenyl-o-toluamide,
k. α-(2,2-dimethylbutanoyl)-N-tert.butyl-α-phenyl-o-toluamide, or
l. N-tert.butyl-α-(1-methyl cyclohexanoyl)-α-phenyl-o-toluamide,
there is obtained
a. 3-tert.butyl-4-(p-chlorophenyl) isocarbostril,
b. 3-tert.butyl-4-(o-tolyl) isocarbostyril,
c. 3-tert.butyl-4p-methoxyphenyl) isocarbostril,
d. 3-tert.butyl-4-(m-trifluoromethylphenyl) isocarbostyril,
e. 3-tert.butyl-4-(3,4-dichlorophenyl) isocarbostyril,
f. 3-tert.butyl-4-(p-tolyl) isocarbostyril,
g. 3-tert.butyl-8-chloro-4-phenyl isocarbostyril,
h. 3-tert.butyl-6-methyl-4-phenyl isocarbostyril,
i. 3-tert.butyl-4-phenyl-7-trifluoromethyl isocarbostyril,
j. 3-tert.butyl-6-methoxy-4-phenyl isocarbostyril
k. 3-(2,2-dimethylbutyl)-4-phenyl isocarbostyril, or
l. 3-1(1-methyl cyclohexyl)-4-phenyl isocarbostyril, respectively.

EXAMPLE 4

3-tert.butyl-1-chloro-4-phenyl isoquinoline

A mixture of 11 g. (0.04 mole) of 3-tert.butyl-4-phenyl isocarbostyril and 40 ml. of phosphorous oxychloride is refluxed for one hour. The excess solvent is removed in vacuo and ice is added to the residue and stirred. The resulting solid is filtered and washed with water and recrystallized from ethanol to give 3-tert.butyl-1-chloro-4-phenyl isoquinoline; m.p. 139°–140° C.

When the above process is carried out and in place of phosphorous oxychloride there is used phosphorous pentachloride or thionyl chloride, the identical product is again obtained.

When the above process is carried out and in place of 3-tert.butyl-4-phenyl isocarbostyril there is used
a. 3-tert.butyl-4-(p-chlorophenyl) isocarbostril,
b. 3-tert.butyl-4-(o-tolyl) isocarbostyril,
c. 3-tert.butyl-4(p-methoxyphenyl) isocarbostril,
d. 3-tert.butyl-4-(m-trifluoromethylphenyl) isocarbostyril,
e. 3-tert.butyl-4-(3,4-dichlorophenyl) isocarbostyrll,
f. 3-tert.butyl-4-(p-tolyl) isocarbostyril,
g. 3-tert.butyl-8-chloro-4-phenyl isocarbostyril,
h. 3-tert.butyl-6-methyl-4-phenyl isocarbostyril,
i. 3-tert.butyl-4-phenyl-7-trifluoromethyl isocarbostyril,
j. 3-tert.butyl-6-methoxy-4-phenyl isocarbostyril
k. 3-(2,2-dimethylbutyl)-4-phenyl isocarbostyril, or
l. 3-1(1-methyl cyclohexyl)-4-phenyl isocarbostyril,
there is obtained
a. 3-tert.butyl-1-chloro-4-(p-chlorophenyl) isoquinoline,
b. 3-tert.butyl-1-chloro-4-(o-tolyl) isoquinoline,
c. 3-tert.butyl-1-chloro-4-(p-methoxyphenyl) isoquinoline,
d. 3-tert.butyl-1-chloro-4(m-trifluoromethylphenyl) isoquinoline,
e. 3-tert.butyl-1-chloro-4-(3,4-dichlorophenyl) isoquinoline,
f. 3-tert.butyl-1-chloro-4-(p-tolyl) isoquinoline,
g. 3-tert.butyl-1,8-dichloro-4-phenyl isoquinoline,
h. 3-tert.butyl-1-chloro-6-methyl-4-phenyl isoquinoline,
i. 3-tert.butyl-1-chloro-4-phenyl-7-trifluoromethyl isoquinoline,
j. 3-tert.butyl-1-chloro-6-methoxy-4-phenyl isoquinoline,
k. 3-(2,2-dimethylbutyl)-1-chloro-4-phenyl isoquinoline, or
l. 3-(1-methylcyclohexyl)-1-chloro-4-phenyl isoquinoline, respectively.

EXAMPLE 5

3-tert.butyl-4-phenyl isoquinoline hydrochloride

A mixture of 21.7 g. (0.073 mole) of 3-tert.butyl-1-chloro-4-phenyl isoquinoline, 4.09 g. (0.073 mole) potassium hydroxide, 1.09g 10% palladium on carbon and 1 liter of ethanol is hydrogenated at room temperature and 50 psi until 1 equivalent of hydrogen is absorbed. The catalyst is filtered off and washed with ethanol, combined ethanol portions are evaporated in vacuo. The residue is dissolved in ethyl ether, washed with water, dried, and filtered and the filtrate treated with gaseous HCl. The resulting white solid is filtered and recrystallized from ethanolethyl ether, washed with water, dried, and filtered and the filtrate treated with gaseous HCl. The resulting white solid is filtered and recrystallized from ethanol-ethyl ether (1:1) to give 3-tert.butyl-4-phenyl isoquinoline hydrochloride; m.p. 236°–238° C.

When the above process is carried out and in place of 3-tert.butyl-1-chloro-4-phenyl isoquinoline there is used
a. 3-tert.butyl-1-chloro-4-(p-chlorophenyl) isoquinoline,
b. 3-tert.butyl-1-chloro-4-(o-tolyl) isoquinoline,
c. 3-tert.butyl-1-chloro-4-(p-methoxyphenyl) isoquinoline,
d. 3-tert.butyl-1-chloro-4(m-trifluoromethylphenyl) isoquinoline,
e. 3-tert.butyl-1-chloro-4-(3,4-dichlorophenyl) isoquinoline,
f. 3-tert.butyl-1-chloro-4-(p-tolyl) isoquinoline,
g. 3-tert.butyl-1,8-dichloro-4-phenyl isoquinoline,
h. 3-tert.butyl-1-chloro-6-methyl-4-phenyl isoquinoline,
i. 3-tert.butyl-1-chloro-4-phenyl-7-trifluoromethyl isoquinoline,
j. 3-tert.butyl-1-chloro-6-methoxy-4-phenyl isoquinoline,
k. 3-(2,2-dimethylbutyl)-1-chloro-4-phenyl isoquinoline, or
l. 3-(1-methylcyclohexyl)-1-chloro-4-phenyl isoquinoline,
there is obtained as the hydrochloride
a. 3-tert.butyl-4-(p-chlorophenyl) isoquinoline,
b. 3-tert.butyl-4-(o-tolyl) isoquinoline,
c. 3-tert.butyl-4-(p-methoxyphenyl) isoquinoline,
d. 3-tert.butyl-4-(m-trifluoromethylphenyl) isoquinoline,
e. 3-tert.butyl-4-(3,4-dichlorophenyl) isoquinoline,
f. 3-tert.butyl-4-(p-tolyl) isoquinoline,
g. 3-tert.butyl-8-chloro-4-phenyl isoquinoline,
h. 3-tert.butyl-6-methyl-4-phenyl isoquinoline,
i. 3-tert.butyl-4-phenyl-7-trifluoromethyl isoquinoline,
j. 3-tert.butyl-6-methoxy-4-phenyl isoquinoline,
k. 3-(2,2-dimethylbutyl)-4-phenyl isoquinoline, or
l. 3-(1-methylcyclohexyl)-4-phenyl isoquinoline, respectively.

EXAMPLE 6

3-tert.butyl-4-phenyl-1,2,3,4-tetrahydroisoquinoline

A mixture of 28.5 g. (0.11 mole) of 3-tert.butyl-4-phenyl isoquinoline, 2.85 g. platinum oxide and 300 ml. of acetic acid is hydrogenated at room temperature and 50 psi until two equivalents of hydrogen are absorbed. The catalyst is filtered off and the acetic acid is evaporated in vacuo. The residue is dissolved in ether, washed with 50% sodium hydroxide, water and saturated sodium chloride solution, dried over magnesium sulfate, filtered and evaporated. The residue is crystallized from petroleum ether to give 3-tert.butyl-4-phenyl-1,2,3,4-tetrahydroisoquinoline; m.p. 79°–81° C.

When the above process is carried out and in place of 3-tert.butyl-4-phenyl isoquinoline there is used
a. 3-tert.butyl-4-(p-chlorophenyl) isoquinoline,
b. 3-tert.butyl-4-(o-tolyl) isoquinoline,
c. 3-tert.butyl-4-(p-methoxyphenyl) isoquinoline,
d. 3-tert.butyl-4-(m-trifluoromethylphenyl) isoquinoline,
e. 3-tert.butyl-4-(3,4-dichlorophenyl) isoquinoline,
f. 3-tert.butyl-4-(p-tolyl) isoquinoline,
g. 3-tert.butyl-8-chloro-4-phenyl isoquinoline,
h. 3-tert.butyl-6-methyl-4-phenyl isoquinoline,
i. 3-tert.butyl-4-phenyl-7-trifluoromethyl isoquinoline,
j. 3-tert.butyl-6-methoxy-4-phenyl isoquinoline,
k. 3-(2,2-dimethylbutyl)-4-phenyl isoquinoline, or
l. 3-(1-methylcyclohexyl)-4-phenyl isoquinoline,
there is obtained
a. 3-tert.butyl-4-(p-chlorophenyl)-1,2,3,4-tetrahydroisoquinoline,
b. 3-tert.butyl-4-(o-tolyl)-1,2,3,4-tetrahydroisoquinoline,
c. 3-tert.butyl-4-(p-methoxyphenyl)-1,2,3,4-tetrahydroisoquinoline,
d. 3-tert.butyl-4-(m-trifluoromethylphenyl)-1,2,3,4-tetrahydroisoquinoline,
e. 3-tert.butyl-4-(3,4-dichlorophenyl)-1,2,3,4-tetrahydroisoquinoline, f. 3-tert.butyl-4-(p-tolyl)-1,2,3,4-tetrahydroisoquinoline,
g. 2-tert.butyl-8-chloro-4-phenyl-1,2,3,4-tetrahydroisoquinoline,
h. 3-tert.butyl-6-methyl-4-phenyl-1,2,3,4-tetrahydroisoquinoline,
i. 3-tert.butyl-4-phenyl-7-trifluoromethyl-1,2,3,4-tetrahydroisoquinoline,
j. 3-tert.butyl-6-methoxy-4-phenyl-1,2,3,4-tetrahydroisoquinoline,
k. 3-(2,2-dimethylbutyl)-4-phenyl-1,2,3,4-tetrahydroisoquinoline, or l. 3-(1-methylcyclohexyl)-4-phenyl-1,2,3,4-tetrahydroisoquinoline, respectively.

The title compound of this example is an effective antidiabetic when orally administered to diabetic animal at a dosage of 100 mg. twice per day.

What is claimed is:

1. A compound of the formula

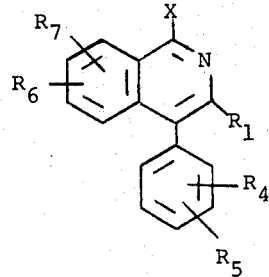

where
$R_1$ represents

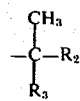

where
$R_2$ and $R_3$ are each, independently, methyl or ethyl, or $R_2$ and $R_3$ together represent $(CH_2)_n$ where
n represents 4, 5 or 6, where
$R_4$, $R_5$, $R_6$, $R_7$ each, independently, represent hydrogen, halo of atomic weight 19–36, trifluoromethyl, lower alkyl having 1–4 carbon atoms, or lower alkoxy having 1–4 carbon atoms, provided that $R_6$ and $R_7$ may not represent said lower alkyl at the 8-position, and provided further that two trifluoromethyl groups or two tertiary butyl groups or a trifluoromethyl group and a tertiary butyl group are not on adjacent carbon atoms.

and

X represents halo of atomic weight about 35–80.

2. The compound of claim 1 which is 3-tert.butyl-1-chloro-4-phenyl-isoquinoline.

* * * * *